(12) United States Patent
Chronis et al.

(10) Patent No.: US 12,303,299 B2
(45) Date of Patent: *May 20, 2025

(54) SYSTEMS AND METHODS FOR DETECTING ATTEMPTED BED EXIT

(71) Applicant: Foresite Healthcare, LLC, Maryland Heights, MO (US)

(72) Inventors: George Chronis, Chesterfield, MO (US); Erik E. Stone, Columbia, MO (US)

(73) Assignee: Foresite Healthcare, LLC, Maryland Heights, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,771

(22) Filed: Jan. 5, 2024

(65) Prior Publication Data

US 2024/0138775 A1    May 2, 2024

Related U.S. Application Data

(63) Continuation of application No. 16/942,479, filed on Jul. 29, 2020, now Pat. No. 11,864,926, which is a
(Continued)

(51) Int. Cl.
*G08B 23/00*    (2006.01)
*A61B 5/00*    (2006.01)
(Continued)

(52) U.S. Cl.
CPC .......... *A61B 5/7275* (2013.01); *A61B 5/1115* (2013.01); *A61B 5/1116* (2013.01);
(Continued)

(58) Field of Classification Search
CPC ... A61B 5/7275; A61B 5/1115; A61B 5/1116; A61B 5/112; A61B 5/1128; A61B 5/746;
(Continued)

(56) References Cited

U.S. PATENT DOCUMENTS

| 4,320,766 A | 3/1982 | Alihanka et al. |
| 5,097,841 A | 3/1992 | Moriuchi et al. |

(Continued)

FOREIGN PATENT DOCUMENTS

| CN | 2394612 Y | 9/2000 |
| CN | 2477135 Y | 2/2002 |

(Continued)

OTHER PUBLICATIONS

Extended European Search Report in EP21849041.5, mailed Aug. 6, 2024, 8 pages.

(Continued)

*Primary Examiner* — Anh V La
(74) *Attorney, Agent, or Firm* — Lewis Rice LLC

(57) ABSTRACT

Systems and methods for identifying someone intending to leave a bed or chair generally before or shortly after the bed or chair is exited. These can allow intervention where necessary to prevent some falls before they occur. The systems and methods typically collect and aggregate real-time patient data to detect "attempted bed exits"—attempts made by a patient which indicate that the patient may be attempting to leave the bed or chair and, determine their risk for falling. Where done in real time, a patient making an "attempt" to exit can be stopped before or shortly after an actual exit is made, permitting staff to assist with, or prevent, the exit as necessary.

16 Claims, 2 Drawing Sheets

Related U.S. Application Data continuation-in-part of application No. 16/255,600, filed on Jan. 23, 2019, now Pat. No. 10,835,186, which is a continuation of application No. 15/248,810, filed on Aug. 26, 2016, now Pat. No. 10,206,630.

(60) Provisional application No. 62/211,472, filed on Aug. 28, 2015.

(51) Int. Cl.
    *A61B 5/11*     (2006.01)
    *G16H 40/67*     (2018.01)
    *G16H 50/20*     (2018.01)
    *G16H 50/30*     (2018.01)

(52) U.S. Cl.
CPC ............ *A61B 5/112* (2013.01); *A61B 5/1128* (2013.01); *G16H 40/67* (2018.01); *G16H 50/20* (2018.01); *A61B 5/746* (2013.01); *A61B 2562/0247* (2013.01); *G16H 50/30* (2018.01)

(58) Field of Classification Search
CPC ........... A61B 2562/0247; G16H 40/67; G16H 50/20; G16H 50/30
USPC ........ 340/573.1, 573.4, 573.7, 540; 600/300, 600/301
See application file for complete search history.

(56) References Cited

U.S. PATENT DOCUMENTS

| | | | |
|---|---|---|---|
| 5,309,921 A | 5/1994 | Kisner et al. | |
| 5,844,488 A | 12/1998 | Musick | |
| 6,002,994 A | 12/1999 | Lane et al. | |
| 6,915,008 B2 | 7/2005 | Barman et al. | |
| 7,420,472 B2 | 9/2008 | Tran | |
| 7,502,498 B2 | 3/2009 | Wen et al. | |
| 7,786,874 B2 | 8/2010 | Rodgers | |
| 7,843,351 B2 | 11/2010 | Bourne et al. | |
| 7,987,069 B2 * | 7/2011 | Rodgers ............... | A61G 7/0509 702/150 |
| 8,287,452 B2 | 10/2012 | Young et al. | |
| 8,444,558 B2 | 5/2013 | Young et al. | |
| 8,547,236 B2 | 10/2013 | Gannot et al. | |
| 8,723,677 B1 | 5/2014 | Kiani | |
| 8,727,981 B2 | 5/2014 | Bechtel et al. | |
| 9,129,506 B1 | 9/2015 | Kusens | |
| 9,510,784 B2 | 12/2016 | Benson et al. | |
| 9,538,158 B1 | 1/2017 | Rush et al. | |
| 9,741,221 B1 | 8/2017 | Rehfeld et al. | |
| 9,782,108 B2 | 10/2017 | Shimizu | |
| 9,795,321 B2 | 10/2017 | Shimizu | |
| 9,814,410 B2 | 11/2017 | Kostic et al. | |
| 9,866,797 B2 | 1/2018 | Clark et al. | |
| 10,078,951 B2 | 9/2018 | Kusens | |
| 10,206,630 B2 | 2/2019 | Stone et al. | |
| 11,819,344 B2 | 11/2023 | Stone et al. | |
| 11,864,926 B2 * | 1/2024 | Chronis ............... | A61B 5/1128 |
| 2001/0020395 A1 | 9/2001 | Hubbard | |
| 2003/0058111 A1 | 3/2003 | Lee et al. | |
| 2003/0059081 A1 | 3/2003 | Trajkovic | |
| 2003/0085992 A1 | 5/2003 | Arpa et al. | |
| 2004/0030531 A1 | 2/2004 | Miller et al. | |
| 2004/0119716 A1 | 6/2004 | Park et al. | |
| 2004/0228503 A1 | 11/2004 | Cutler | |
| 2005/0088515 A1 | 4/2005 | Geng | |
| 2005/0094879 A1 | 5/2005 | Harville | |
| 2005/0124864 A1 | 6/2005 | Mack et al. | |
| 2005/0190062 A1 | 9/2005 | Sullivan et al. | |
| 2006/0042409 A1 | 3/2006 | Nemoto | |
| 2006/0055543 A1 | 3/2006 | Ganesh et al. | |
| 2006/0152378 A1 | 7/2006 | Lokhorst et al. | |
| 2007/0003146 A1 | 1/2007 | Ko et al. | |
| 2007/0085690 A1 | 4/2007 | Tran | |
| 2007/0152837 A1 | 7/2007 | Bischoff et al. | |
| 2007/0262247 A1 | 11/2007 | Becerra et al. | |
| 2007/0263900 A1 | 11/2007 | Medasani et al. | |
| 2007/0268480 A1 | 11/2007 | Kaye | |
| 2008/0077020 A1 | 3/2008 | Young et al. | |
| 2008/0117060 A1 | 5/2008 | Cuddihy et al. | |
| 2008/0169931 A1 | 7/2008 | Gentry et al. | |
| 2009/0079559 A1 | 3/2009 | Dishongh et al. | |
| 2009/0079813 A1 | 3/2009 | Hildreth | |
| 2009/0089089 A1 | 4/2009 | Jang et al. | |
| 2009/0141124 A1 | 6/2009 | Liu et al. | |
| 2009/0178199 A1 | 7/2009 | Brauers et al. | |
| 2009/0243833 A1 | 10/2009 | Huang et al. | |
| 2010/0049095 A1 | 2/2010 | Bunn et al. | |
| 2010/0152546 A1 | 6/2010 | Behan et al. | |
| 2010/0163315 A1 | 7/2010 | York et al. | |
| 2010/0171622 A1 | 7/2010 | Brauers et al. | |
| 2010/0256512 A1 | 10/2010 | Sullivan | |
| 2010/0302043 A1 | 12/2010 | Skubic et al. | |
| 2010/0330543 A1 | 12/2010 | Black et al. | |
| 2011/0054330 A1 | 3/2011 | Pfeiffer et al. | |
| 2011/0087113 A1 | 4/2011 | Mack et al. | |
| 2011/0306844 A1 | 12/2011 | Young | |
| 2011/0308015 A1 | 12/2011 | Newham | |
| 2012/0019643 A1 | 1/2012 | Gideon et al. | |
| 2012/0030231 A1 | 2/2012 | Cropper | |
| 2012/0053423 A1 | 3/2012 | Kenalty et al. | |
| 2012/0075464 A1 | 3/2012 | Derenne et al. | |
| 2012/0101411 A1 | 4/2012 | Hausdorff et al. | |
| 2012/0123279 A1 | 5/2012 | Brueser et al. | |
| 2012/0130202 A1 | 5/2012 | Jain | |
| 2012/0172681 A1 | 7/2012 | Sun et al. | |
| 2012/0253201 A1 | 10/2012 | Reinhold | |
| 2012/0327218 A1 | 12/2012 | Baker et al. | |
| 2013/0030825 A1 | 1/2013 | Bagwandeen et al. | |
| 2013/0127620 A1 | 5/2013 | Siebers et al. | |
| 2013/0267791 A1 | 10/2013 | Halperin et al. | |
| 2013/0342691 A1 | 12/2013 | Lewis et al. | |
| 2014/0022079 A1 * | 1/2014 | Wilson .................. | G16H 40/20 340/573.1 |
| 2014/0022081 A1 | 1/2014 | Ribble et al. | |
| 2014/0081654 A1 | 3/2014 | Bechtel et al. | |
| 2014/0139616 A1 | 5/2014 | Pinter et al. | |
| 2014/0303460 A1 | 10/2014 | Corley et al. | |
| 2014/0307056 A1 | 10/2014 | Collet Romea et al. | |
| 2014/0330172 A1 | 11/2014 | Jovanov et al. | |
| 2015/0025327 A1 | 1/2015 | Young et al. | |
| 2015/0094597 A1 | 4/2015 | Mestha et al. | |
| 2015/0109442 A1 | 4/2015 | Derenne | |
| 2015/0112151 A1 | 4/2015 | Muhsin et al. | |
| 2015/0164238 A1 | 6/2015 | Benson et al. | |
| 2015/0254956 A1 * | 9/2015 | Shen ..................... | A61B 5/445 340/573.1 |
| 2015/0302310 A1 | 10/2015 | Wernevi et al. | |
| 2015/0320339 A1 | 11/2015 | Larson et al. | |
| 2015/0323388 A1 | 11/2015 | Kostic et al. | |
| 2016/0089059 A1 | 3/2016 | Hu | |
| 2016/0140307 A1 | 5/2016 | Brosnan et al. | |
| 2016/0140827 A1 | 5/2016 | Derenne et al. | |
| 2016/0150966 A1 | 6/2016 | Heinrich et al. | |
| 2016/0203694 A1 | 7/2016 | Högasten et al. | |
| 2016/0206216 A1 | 7/2016 | Kirenko | |
| 2016/0217260 A1 | 7/2016 | Aarts et al. | |
| 2016/0267327 A1 | 9/2016 | Franz et al. | |
| 2017/0024874 A1 | 1/2017 | Pang et al. | |
| 2017/0053401 A1 | 2/2017 | Hata et al. | |
| 2017/0055888 A1 | 3/2017 | Matsumoto et al. | |
| 2017/0055917 A1 | 3/2017 | Stone et al. | |
| 2017/0109391 A1 | 4/2017 | Rosen et al. | |
| 2017/0330044 A1 | 11/2017 | Telpaz et al. | |
| 2017/0344832 A1 | 11/2017 | Leung et al. | |
| 2018/0192007 A1 | 7/2018 | Clark et al. | |
| 2018/0192923 A1 | 7/2018 | Fu et al. | |
| 2019/0150852 A1 | 5/2019 | Stone et al. | |

(56) References Cited

U.S. PATENT DOCUMENTS

| | | | |
|---|---|---|---|
| 2019/0349554 | A1 | 11/2019 | Derenne et al. |
| 2020/0211154 | A1 | 7/2020 | Ng et al. |

FOREIGN PATENT DOCUMENTS

| | | | |
|---|---|---|---|
| CN | 101499106 A | | 8/2009 |
| CN | 101953740 A | | 1/2011 |
| CN | 202101963 U | | 1/2012 |
| DE | 10305289 A1 | | 8/2004 |
| DE | 102008011142 A1 | | 8/2009 |
| DE | 102008058781 A1 | | 6/2010 |
| FR | 2865032 A1 | | 7/2005 |
| GB | 2445760 A1 | | 7/2008 |
| HR | P20041063 A9 | | 6/2007 |
| JP | 2006288932 A | | 10/2006 |
| NL | 8701288 A | | 1/1989 |
| WO | 2008048078 A1 | | 4/2008 |
| WO | 2013033524 A2 | | 3/2013 |
| WO | 2013058985 A1 | | 4/2013 |
| WO | 2013066601 A1 | | 5/2013 |

OTHER PUBLICATIONS

Anderson et al., "Recognizing Falls from Silhouettes," Proceedings of the 28th IEEE, Engineering in Medicine and Biology Society Annual International Conference, Aug. 30-Sep. 3, 2006, New York City, USA, pp. 6388-6391.

Bujnoch, Z., "Video Games and Healthcare: Bridging the Gap between Patient and Consumer," Mastering the Art and Science of Patient Adherence, Dec. 19, 2011, 3 pages.

Davis et al., "Toward 3-D Gesture Recognition," Research supported by the National Science Foundation grants CDA-9200369, IRI-9122006 and IRI-9220768, Feb. 2004, 16 pages.

Harvey et al., "Speedup of Fuzzy Logic through Stream Processing on Graphics Processing Units," Proceedings: IEEE Congress on Evolutionary Computation, 2008, pp. 3809-3815.

Heise et al., "Monitoring Pulse and Respiration with a Non-Invasive Hydraulic Bed Sensor," 32nd Annual International Conference of the IEEE Engineering in Medicine and Biology Society, Aug. 31-Sep. 4, 2010, Buenos Aires, Argentina, pp. 2119-2123.

Heise et al., "Refinement and Evaluation of a Hydraulic Bed Sensor," 33rd Annual International Conference of the IEEE Engineering in Medicine and Biology Society, Aug. 30-Sep. 3, 2011, Boston, Massachusetts, USA, pp. 4356-4360.

International Search Report and Written Opinion in PCT/US2021/043752, mailed Nov. 25, 2021, 7 pages.

Kepski et al., "Unobtrusive Fall Detection at Home Using Kinect Sensor," Computer Analysis of Images and Patterns, Aug. 27-29, 2013, Part 1, pp. 457-464.

Mack et al., "Development and Preliminary Validation of Heart Rate and Breathing Rate Detection Using a Passive, Ballistocardiography-Based Sleep Monitoring System," IEEE Transactions on Information Technology in Biomedicine, Jan. 2009, vol. 13, No. 1, pp. 111-120.

Martin et al., "Gait Initiation in Community-Dwelling Adults with Parkinson Disease: Comparison with Older and Younger Adults without the Disease," Physical Therapy, Jun. 2002, vol. 82, No. 6, pp. 566-577.

Prohemon, "Proactive Health Monitoring: Final report of the research project in the Academy of Finland Proactive Computing research program," ProHeMon final report, Feb. 3, 2006, 14 pages.

Rosales et al., "Heartbeat Detection from a Hydraulic Bed Sensor Using a Clustering Approach," 34th Annual International Conference of the IEEE Engineering in Medicine and Biology Society, Aug. 28-Sep. 1, 2012, San Diego, California, USA, pp. 2383-2387.

Rosales, L., "Exploring Passive Heartbeat Detection Using a Hydraulic Bed Sensor System," Master's Thesis, Dec. 2011, University of Missouri—Columbia, 172 pages.

Shin et al., "Automatic Ballistocardiogram (BCG) Beat Detection Using a Template Matching Approach," 30th Annual International IEEE Engineering in Medicine and Biology Society Conference, Aug. 20-24, 2008, Vancouver, British Columbia, Canada, pp. 1144-1146.

Skala et al., "4D Thermal Imaging System for Medical Applications," Periodicum Biologorum, Nov. 2011, vol. 113, No. 4, pp. 407-416.

Skubic et al., "Testing Non-Wearable Fall Detection Methods in the Homes of Older Adults," 2016 38th Annual International Conference of the IEEE Engineering in Medicine and Biology Society (EMBC), Aug. 16, 2016, pp. 557-560.

Sledge et al., "Emergent Trend Detection in Diurnal Activity," 30th Annual International IEEE Engineering in Medicine and Biology Society Conference, Aug. 20-24, Vancouver, British Columbia, Canada, pp. 3815-3818.

Wall et al., "The Timed Get-up-and-go Test Revisited: Measurement of the Component Tasks," Journal of Rehabilitation Research and Development, Jan.-Feb. 2000, vol. 37, No. 1, pp. 109-114.

Wang et al., "Development of a PVDF Piezopolymer Sensor for Unconstrained In-Sleep Cardiorespiratory Monitoring," Journal of Intelligent Material Systems and Structures, Mar. 2003, vol. 14, No. 3, pp. 185-190.

Watanabe et al., "Noninvasive Measurement of Heartbeat, Respiration, Snoring and Body Movement of a Subject in Bed via Pneumatic Method," IEEE Transactions on Biomedical Engineering, Dec. 2005, vol. 52, No. 12, pp. 2100-2107.

Wikipedia, "Thermographic camera," Wikipedia.org, updated Jul. 10, 2014, Retrieved from Internet: <https://en.wikipedia.org/w/index.php?title=Thermographic_camera&oldid=616310920>, 8 pages.

Yaguchi et al., "Arbitrary Viewpoint Video Synthesis from Multiple Uncalibrated Cameras," IEEE Transactions on Systems, Man, and Cybernetics—Part B: Cybernetics, Feb. 2004, vol. 34, No. 1, pp. 430-439.

Zhu et al., "Real-Time Monitoring of Respiration Rhythm and Pulse Rate During Sleep," IEEE Transactions on Biomedical Engineering, Dec. 2006, vol. 53, No. 12, pp. 2553-2563.

\* cited by examiner

SYSTEMS AND METHODS FOR DETECTING ATTEMPTED BED EXIT

CROSS-REFERENCE TO RELATED APPLICATION(S)

This application is a Continuation of U.S. patent application Ser. No. 16/942,479, filed Jul. 29, 2020, which is a Continuation-In-Part of U.S. patent application Ser. No. 16/255,600 filed Jan. 23, 2019, issued as U.S. Pat. No. 10,835,186, which is a Continuation of U.S. patent application Ser. No. 15/248,810, filed Aug. 26, 2016, issued as U.S. Pat. No. 10,206,630, which in turn claims benefit of U.S. Provisional Patent Application No. 62/211,472, filed Aug. 28, 2015.

BACKGROUND OF THE INVENTION

Field of the Invention

This invention is related to the field of healthcare services, including but not limited to hospital and long-term care, and particularly to systems and methods aimed at increasing the efficiency in the utilization of services and resources and decreasing the risk of serious injury and death by inhibiting falls.

Description of the Related Art

One of the most dangerous things for patients in an acute health care setting (like a hospital), in a chronic health care setting (like a skilled nursing facility), and even at home, is the danger of falls from a chair or bed. This is particularly true for the elderly, as falls are the leading cause of injury for adults over the age of 65, with the risk increasing with each additional year of age. By some estimates, approximately one-third of the elderly will suffer some sort of fall each year, and of those, approximately one fourth (25%) to one third (33%) will suffer moderate or severe injuries.

Even more concerning, those injuries can directly or indirectly result in death. Directly, falls result in more than 30,000 deaths annually in the United States (400,000 worldwide) in individuals over the age of 65, with "accidents," including falls, representing the eighth leading cause of death, in large part due to the risk of traumatic brain injury which can occur during a fall. Indirectly, falls can result in decreased independence, increased pain, reduced mobility, and an overall reduction in quality of life. These, along with the possible need for surgery and pain relief medication have each been paired with an overall reduction in life expectancy. Thus, fall prevention and inhibition in the elderly has become an important issue for care facilities of all types.

Falls are not limited to the elderly, however, and even otherwise able-bodied individuals are a higher risk of falls in healthcare settings particularly following medical procedures, accidents, heart attacks, or other non-fall events. Procedures, treatments, and medications (including pain killers) can make patients confused and dizzy and can cause bouts of semi-consciousness, nausea, or vertigo, increasing risk of falls. This risk is in addition to any increased risk due to whatever condition or event lead to the acute stay, which may already be causing muscle weakness, poor cardiovascular or pulmonary function, visual accuracy problems, pain, or other issues.

Further, even the individual's presence in a hospital, skilled nursing facility, or other healthcare environment on its own increases the risk of falls. For sanitary purposes and ease of cleaning, floors in these facilities are typically tiled—smooth hard surfaces without the cushioning of carpet—and often slippery. Rooms are often filled with equipment, including cords, tubes, and wires, adding additional dangers to even a short walk to a restroom. Perhaps most obviously—these facilities are not a "home environment" for most patients, and so any reduction to falls as a result of familiarity is lost.

In an acute healthcare setting, falls can prolong otherwise short-term stays in a healthcare environment, while exacerbating already existing conditions in chronic healthcare settings. As a result, healthcare facilities take considerable care in assessing fall risks and in providing, where possible, beds which can detect attempted bed exits, with the goal of preventing falls before they occur. While this care is certainly out of concern for patients, there are financial reasons as well. Falls for hospitalized patients are believed to present 30-40% of safety incidents within any hospital and will generally occur at a rate of 4-14 for every 1,000 bed days at a hospital. For even a relatively small facility, this can lead to multiple fall incidents every month, and can be a daily occurrence for a large institution. The problem is exacerbated because falls are often seen as preventable and, therefore, falls can result in penalty to the hospital in the form of reduced governmental recognition for quality of care and malpractice lawsuits.

Beginning in October 2008, Medicare stopped reimbursing hospitals for specific instances of this kind of "error." The Centers for Medicare & Medicaid Services drew up a list of 'reasonably preventable' mistakes, termed 'never-events'. After that date, falls in hospitals were no longer reimbursed by Medicare. On Jun. 1, 2011, Medicaid followed Medicare's lead in no longer reimbursing hospitals for 'never-events', including falls. Additionally, the Affordable Care Act imposes payment penalties on the twenty-five percent (25%) of hospitals whose rates of hospital-acquired injuries due to falls are the highest.

To counter this, bed exit alarms have been used. Where a patient has been deemed a fall risk, the patient can be placed in a bed, either with a bed exit alarm affixed to it, or in a bed that has a bed exit alarm which was incorporated into the bed at the time of manufacture. When a patient exits a bed where an alarm is installed, an alarm goes off.

The most obvious problem with existing bed exit alarms is that they do not solve the problem of preventing or inhibiting falls after arising from a bed or chair. Instead, they merely detect that a patient has left their bed and therefore can detect that there is an increased risk of fall. While a patient that has left their bed is clearly at an increased risk for a fall, they are at risk for such fall the instant they leave their bed. Thus, existing bed exit alarms effectively act to notify personnel that an individual is at a dramatically heightened fall risk only after they are at such risk. As an individual with a true risk of fall is very likely to fall quickly after leaving their bed or chair or even as they are leaving it (before they have even had a chance to ambulate), by the point a prior alarm goes off, the fall (and resulting damage) is likely done. Thus, these systems act more to detect that a fall has occurred, than to inhibit the likelihood of one occurring in the first place. While fall detection is valuable to reduce risk of long term damage form the fall due to quick response, the fundamental problem of not inhibiting the fall in the first place, is left unsolved by prior systems and this goes a long way to explain why conventional systems only decrease falls by about twenty percent (20%) according to current statistics.

Bed exit alarm systems also have other flaws. First, they suffer from a significant rate of false negatives—alarms failing to go off when a patient has exited, which obviously defeats the purpose. They also suffer from substantial false positives—alarms going off when a patient has not left bed but is instead just moving or rolling over, or even just sitting up for a bit. These must be treated as true positives and investigated, taxing healthcare employee resources.

Further, where a facility does not provide alarms on every bed, staff must also attempt to assess those patients with the greatest need, which should correlate with fall risk and provide alarm system beds to those patients to most effectively reduce the incidence of falls at the facility overall. However, most fall risk assessments are highly subjective, based upon either the individual's own perceptions of their risk, or the perceptions of health care employees, which may be based upon a limited history. Even where assessments are grounded upon more objective criteria, they are often based upon an individual's prior medical history, which may (or may not) be indicative of their risk of falling at the current time. In effect, the fall risk assessment in prior systems is actually determining who needs assistance and the bed alarm is simply trying to indicate when.

In general, this combination, coupled with a healthcare facility's very reasonable desire to decrease liability, causes facilities to potentially overestimate falling risk, resulting in patients often being confined to wheelchairs or beds when perhaps they do not need to be, receiving assistance from staff every time they wish to leave bed, and with staff being bogged down taking regular reassessments of patients. These significantly drain staffing resources. Further, as reassessments are time consuming and ordered with a regularity (often every four to eight hours) that prevents any real change from being documentable, such reassessments become a low priority for overly tasked medical staff, and are often not performed or not performed well, making them ineffective.

The alternative is to have bed exit alarms placed upon every bed. While this removes concerns of effectively triaging patients and providing alarms only to those patients at the highest risk (or perceived highest risk) of falling, it does so at great cost, and would also lead to a substantial number of false positives (alarms going off where there is no bed exits) and true positives (people exiting beds) where there are no substantial concerns of the patient falling. While the latter issue can be somewhat improved by manually turning certain alarms off for patients with less risk, this obviously defeats the purpose of having universal alarms installed in the first place, and effectively returns the "every bed" option to one of using alarms based upon subjective analysis only on certain beds.

SUMMARY OF THE INVENTION

Because of these and other problems in the art, what is needed are systems and methods for identifying someone intending to leave a bed or chair before the bed or chair is exited, evaluated in real time, to allow intervention where necessary to prevent falls before they occur. These are referred to herein as "attempted" bed exits where the user attempts to exit the bed, but where intervention can preferably be supplied before they actually do so. With regards to this, described herein, among other things, are systems and methods that collect and aggregate real-time patient data to detect "attempted bed exits"—attempts made by a patient which indicate that the patient may be attempting to leave the bed or chair and, thus, place themselves at risk for falling. Where done in real time, a patient making an "attempt" to exit can be stopped before an actual exit is made, permitting staff to assist with, or prevent, the exit as necessary. Further, systems and methods will preferably evaluate the danger of falling after a particular bed exit, that is the current attempt being successful, as opposed to simply determining the risk of the patient generally.

There is described herein, among other things, a system for determining the risk of a patient falling after exiting a bed, the system comprising: a bed including a bed sensor for monitoring a bed is occupied by a patient; a depth camera for imaging the patient; and a computer running appropriate software to: determine movement specifics of how the patient moves immediately prior to exiting the bed from the bed sensor and the depth camera; based on the movement specifics, evaluate a patient's instantaneous risk of falling after exiting the bed; and if the instantaneous risk is sufficiently high, issuing an alert for the patient.

In an embodiment of the system, the computer determines from the bed sensor that the patient is attempting to get up.

In an embodiment of the system, the computer obtains from the bed sensor the amount of time it takes the patient to go from a prone to a sitting position.

In an embodiment of the system, the computer obtains from the bed sensor the amount of time it takes the patient to go from a sitting to a standing position.

In an embodiment of the system, the computer obtains from the bed sensor at least on of the patient's current heart rate, respiration, or body temperature.

In an embodiment of the system, the computer determines from the depth sensor if an assistive device of the patient is within reach of the patient.

In an embodiment of the system, the computer determines from the depth sensor if the patient is connected to an IV line.

In an embodiment of the system, the computer determines from the depth sensor that the patient is attempting to get up.

In an embodiment of the system, the computer obtains from the depth sensor the amount of time it takes the patient to go from a prone to a sitting position.

In an embodiment of the system, the computer obtains from the depth sensor the amount of time it takes the patient to go from a sitting to a standing position.

In an embodiment of the system, the computer compares data from the bed sensor to historical data for the patient.

In an embodiment of the system, the computer compares data from the depth sensor to historical data for the patient.

In an embodiment of the system, the historical data was generated from the patient previously walking before entering the bed.

In an embodiment of the system, the computer compares data from the bed sensor to data for patients who previously fell.

In an embodiment of the system, the computer compares data from the depth sensor to data for patients who previously fell.

In an embodiment of the system, the computer evaluates data from the depth sensor to determine the individuals walking speed.

In an embodiment of the system, the computer evaluates data from the depth sensor to determine the individuals gait while walking.

In an embodiment of the system, the alert is made to medical personnel caring for the patient.

In an embodiment of the system, the alert is made to the patient.

There is also described herein, in an embodiment, a method for determining the risk of a patient falling after exiting a bed, the method comprising: providing a bed including a bed sensor for monitoring a bed is occupied by a patient; providing a depth camera for imaging the patient; determining movement specifics of how the patient moves immediately prior to exiting the bed from the bed sensor and the depth camera; based on the movement specifics, evaluating a patient's instantaneous risk of falling after exiting the bed; and if the instantaneous risk is sufficiently high, issuing an alert for the patient.

DESCRIPTION OF THE PREFERRED EMBODIMENT(S)

Figure 1:
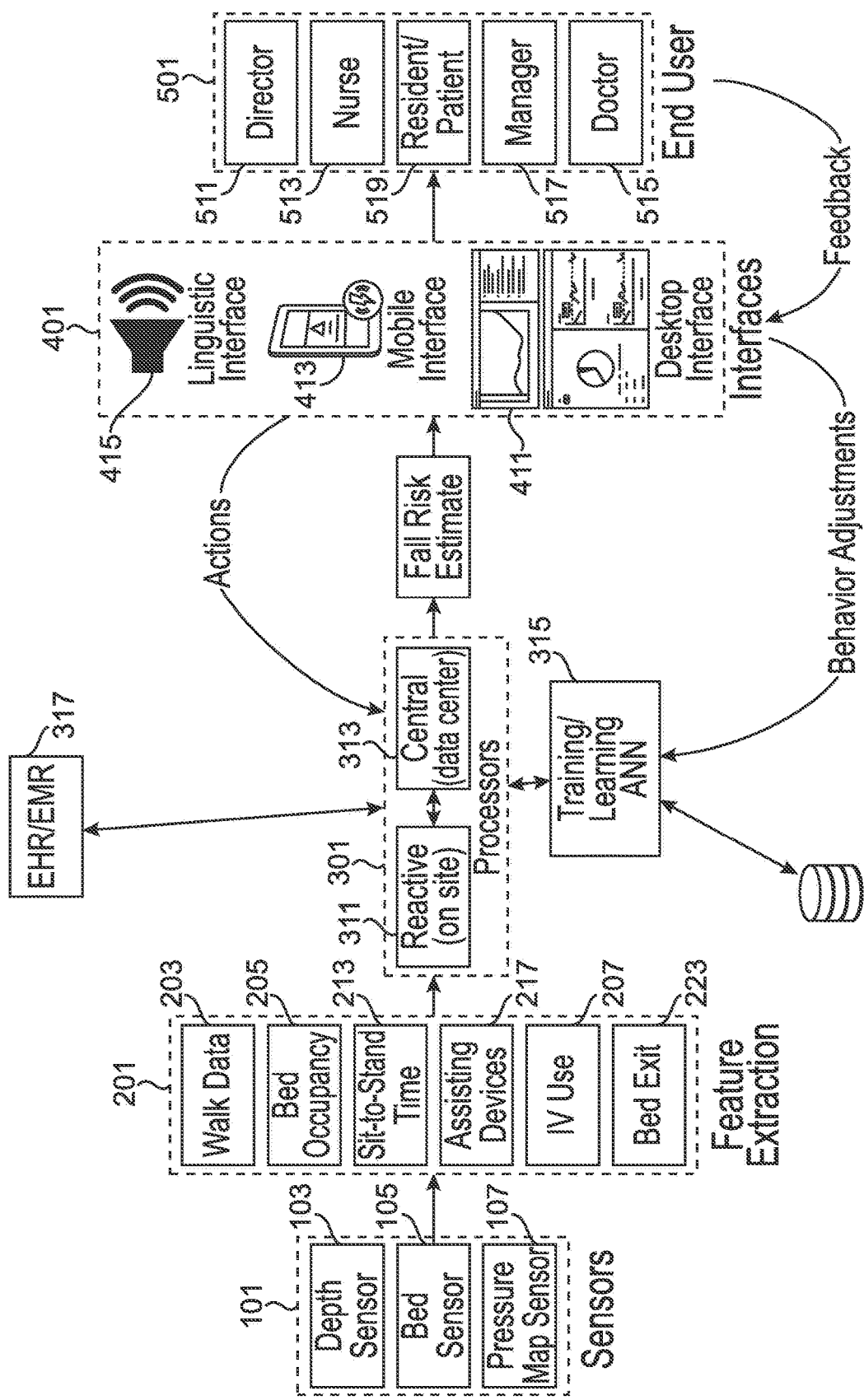
FIG. 1 depicts a system for implementing the intelligent admissions systems and methods described herein.

The systems and methods herein generally utilize objective standards for evaluating various factors to determine a person's current and ongoing fall risk, while also evaluating their instantaneous likelihood of making a bed exit. The systems and methods used herein will generally utilize machine observations and calculations during an attempted bed exit so as to eliminate much of the potential bias or relative skill that is currently used in conjunction with human observations and evaluations prior to a specific bed exit. However, while every patient is preferably assessed for risk, in an embodiment the system the methods may only provide alerts for patients where a subjective heightened risk for falls has been previously identified to save resources.

In an embodiment, the systems and methods may issue warnings before the exit occurs, or detect the exit condition as it occurs, and alert against such conditions. These warnings may be used as notifications for healthcare personnel (for example, to initiate an additional action such as sending a nurse to the patient to assist), as notifications for the patient themselves (for example, triggering a warning to the patient to wait for assistance), or may trigger automatic mechanical responses to inhibit the attempt or assist in the exit (for example to raise a bed rail or to move a walker closer to the bed). The systems and methods may provide monitoring, assessment, and alerts to enable healthcare professionals to proactively intervene, and potentially prevent, adverse health events, including falls. However, these systems and methods need not be confined to healthcare facilities, and can be used in a home setting to alert healthcare workers, aides, or family members in situations where fall risk is deemed to be a concern.

The systems and methods described herein generally include the use of computers to collect and examine data concerning potential patients both prior to admission and during such patient's stay. The system may operate without the need for additional, external information or may operate in conjunction with information provided from other sources. In an embodiment, the systems and methods use factors such as, but not necessarily limited to, bed occupancy, patient weight, patient mass, patient walks, patient height, specific patient capability (for example, a known injury to a leg or foot), and/or gait data extracted or developed automatically using sensors, or sensor systems. It may also include factors which include a lack of bed exits for a certain amount of time (which puts the patient at higher risk), a patient's typical use of an assisting device (such as a cane or walker) to exit the bed or while ambulating, possible tethering of the patient to an IV or monitoring device, the sit-to-stand time normal for this patient in exiting a bed or standing from a chair, the characteristics of their first walk or current steps, the characteristics of movement of a patient on the bed while trying to exit the bed, or a combination of some or all of the above. Data may also be combined in from other sources and materials such as pharmacological data for medications a patient may be on (e.g. those that are known to cause dizziness), data from Electronic Medical Records (EMRs) such as, but not limited to, vital signs or known risk factors for falling, or from third party wearables or other sensors such as fitness trackers. As additional data is obtained, it is either combined with prior data points using an algorithm, or where appropriate, directly used to adjust calculations for what constitutes an attempted bed exit.

Sensors and sensor systems suitable for data collection of the above may include, but are not necessarily limited to: the integrated sensor network described in U.S. Utility patent application Ser. No. 12/791,628, filed Jun. 1, 2010, the entire disclosure of which is incorporated herein by reference; the anonymized video analysis methods and systems described in U.S. Utility patent application Ser. No. 12/791,496, filed Jun. 1, 2010, the entire disclosure of which is incorporated herein by reference; the hydraulic bed sensor and system for non-invasive monitoring of physiological data described in U.S. Utility patent application Ser. No. 13/600,539, filed Aug. 31, 2012, the entire disclosure of which is incorporated herein by reference; and the accelerometer-based bed and related sensors described in U.S. Provisional Patent Application No. 63/008,396, the entire disclosure of which is incorporated herein by reference.

Such sensors and sensor systems may include, but are not necessarily limited to, the activity analysis, fall detection and risk assessment systems and methods described in U.S. Utility patent application Ser. No. 13/871,816, filed Apr. 26, 2013, and Ser. No. 14/169,508, filed Jan. 31, 2014, the entire disclosure of which is incorporated herein by reference. In particular, the '508 application describes the use of depth image data from at least one depth camera associated with a particular patient, and generating at least one three-dimensional object based on the depth image data. See, e.g., FIGS. 1-5, and paragraphs 22-57, describing same.

Throughout this disclosure, the term "computer" describes hardware which generally implements functionality provided by digital computing technology, particularly computing functionality associated with microprocessors. The term "computer" is not intended to be limited to any specific type of computing device, but it is intended to be inclusive of all computational devices including, but not limited to: processing devices, microprocessors, personal computers, desktop computers, laptop computers, workstations, terminals, servers, clients, portable computers, handheld computers, cell phones, mobile phones, smart phones, tablet computers, server farms, hardware appliances, minicomputers, mainframe computers, video game consoles, handheld video game products, and wearable computing devices including but not limited to eyewear, wristwear, pendants, fabrics, and clip-on devices.

As used herein, a "computer" is necessarily an abstraction of the functionality provided by a single computer device outfitted with the hardware and accessories typical of computers in a particular role. By way of example and not limitation, the term "computer" in reference to a laptop computer would be understood by one of ordinary skill in the art to include the functionality provided by pointer-based input devices, such as a mouse or track pad, whereas the term "computer" used in reference to an enterprise-class server would be understood by one of ordinary skill in the art to include the functionality provided by redundant systems, such as RAID drives and dual power supplies.

It is also well known to those of ordinary skill in the art that the functionality of a single computer may be distributed across a number of individual machines. This distribution may be functional, as where specific machines perform specific tasks; or, balanced, as where each machine is capable of performing most or all functions of any other machine and is assigned tasks based on its available resources at a point in time. Thus, the term "computer" as used herein, can refer to a single, standalone, self-contained device or to a plurality of machines working together or independently, including without limitation: a network server farm, "cloud" computing system, software-as-a-service, or other distributed or collaborative computer networks.

Those of ordinary skill in the art also appreciate that some devices which are not conventionally thought of as "computers" nevertheless exhibit the characteristics of a "computer" in certain contexts. Where such a device is performing the functions of a "computer" as described herein, the term "computer" includes such devices to that extent. Devices of this type include but are not limited to: network hardware, print servers, file servers, NAS and SAN, load balancers, and any other hardware capable of interacting with the systems and methods described herein in the matter of a conventional "computer."

As will be appreciated by one skilled in the art, some aspects of the present disclosure may be embodied as a system, method or process, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable media having computer readable program code embodied thereon.

Any combination of one or more computer readable media may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Throughout this disclosure, the term "software" refers to code objects, program logic, command structures, data structures and definitions, source code, executable and/or binary files, machine code, object code, compiled libraries, implementations, algorithms, libraries, or any instruction or set of instructions capable of being executed by a computer processor, or capable of being converted into a form capable of being executed by a computer processor, including without limitation virtual processors, or by the use of run-time environments, virtual machines, and/or interpreters. Those of ordinary skill in the art recognize that software can be wired or embedded into hardware, including without limitation onto a microchip, and still be considered "software" within the meaning of this disclosure. For purposes of this disclosure, software includes without limitation: instructions stored or storable in RAM, ROM, flash memory BIOS, CMOS, mother and daughter board circuitry, hardware controllers, USB controllers or hosts, peripheral devices and controllers, video cards, audio controllers, network cards, Bluetooth® and other wireless communication devices, virtual memory, storage devices and associated controllers, firmware, and device drivers. The systems and methods described here are contemplated to use computers and computer software typically stored in a computer- or machine-readable storage medium or memory.

Program code embodied on a computer readable medium may be transmitted using any appropriate medium, including but not limited to wireless, wireline, optical fiber cable, RF, etc., or any suitable combination of the foregoing.

Throughout this disclosure, the term "network" generally refers to a voice, data, or other telecommunications network over which computers communicate with each other. The term "server" generally refers to a computer providing a service over a network, and a "client" generally refers to a computer accessing or using a service provided by a server over a network. Those having ordinary skill in the art will appreciate that the terms "server" and "client" may refer to hardware, software, and/or a combination of hardware and software, depending on context. Those having ordinary skill in the art will further appreciate that the terms "server" and "client" may refer to endpoints of a network communication or network connection, including but not necessarily limited to a network socket connection. Those having ordinary skill in the art will further appreciate that a "server" may comprise a plurality of software and/or hardware servers delivering a service or set of services. Those having ordinary skill in the art will further appreciate that the term "host" may, in noun form, refer to an endpoint of a network communication or network (e.g., "a remote host"), or may, in verb form, refer to a server providing a service over a network ("hosts a website"), or an access point for a service over a network.

Throughout this disclosure, the term "real time" refers to software operating within operational deadlines for a given event to commence or complete, or for a given module, software, or system to respond, and generally invokes that the response or performance time is, in ordinary user perception and considered the technological context, effectively generally cotemporaneous with a reference event. Those of ordinary skill in the art understand that "real time" does not literally mean the system processes input and/or responds instantaneously, but rather that the system processes and/or responds rapidly enough that the processing or response time is within the general human perception of the passage of real time in the operational context of the program. Those of ordinary skill in the art understand that, where the operational context is a graphical user interface, "real time" normally implies a response time of no more than one second of actual time, with milliseconds or microseconds being preferable. However, those of ordinary skill in the art also understand that, under other operational contexts, a system operating in "real time" may exhibit delays longer than one second, particularly where network operations are involved.

The present system is generally designed to provide information to a user that will allow a user to act on it in a certain proscribed manner. Specifically, to reduce a risk of injury from a fall by creating an accurate fall risk assessment at the time of an attempted bed exit for the risk associated with that bed exit. From the assessment, one can then ascertain whether certain movements constitute an attempted bed exit, the risk of that bed exit and, if an intervention before the exit occurs is deemed necessary to reasonably inhibit an enhanced likelihood of fall, implement the intervention. At the same time, the systems can also limit the need to overly restrict behavior to inhibit falls. Those with sufficiently low falling risk can be allowed freedom of movement.

As the system and methods allow for the determination of instantaneous fall risk and can incorporate that information into an analysis of attempted bed exits, attempted bed exits for at-risk individuals can be responded to quickly without overly taxing resources, permitting intervention to prevent falls before they occur, while still allowing for generally increased freedom of motion (and improved quality of life) for most of the patient population.

As discussed herein, the system and methods utilize fall risk information to determine and evaluate attempted bed exits by a patient in a hospital setting, a resident in a senior care community, or a person in a home setting. That is, the systems and methods operate within a controlled environment and as such relate to predicting the likelihood of a fall while the patient is within that environment. While this is not required and any setting can utilize the systems and methods, these settings generally provide concerns for increased fall risk where attempted bed exits are most critical.

Figure 2:
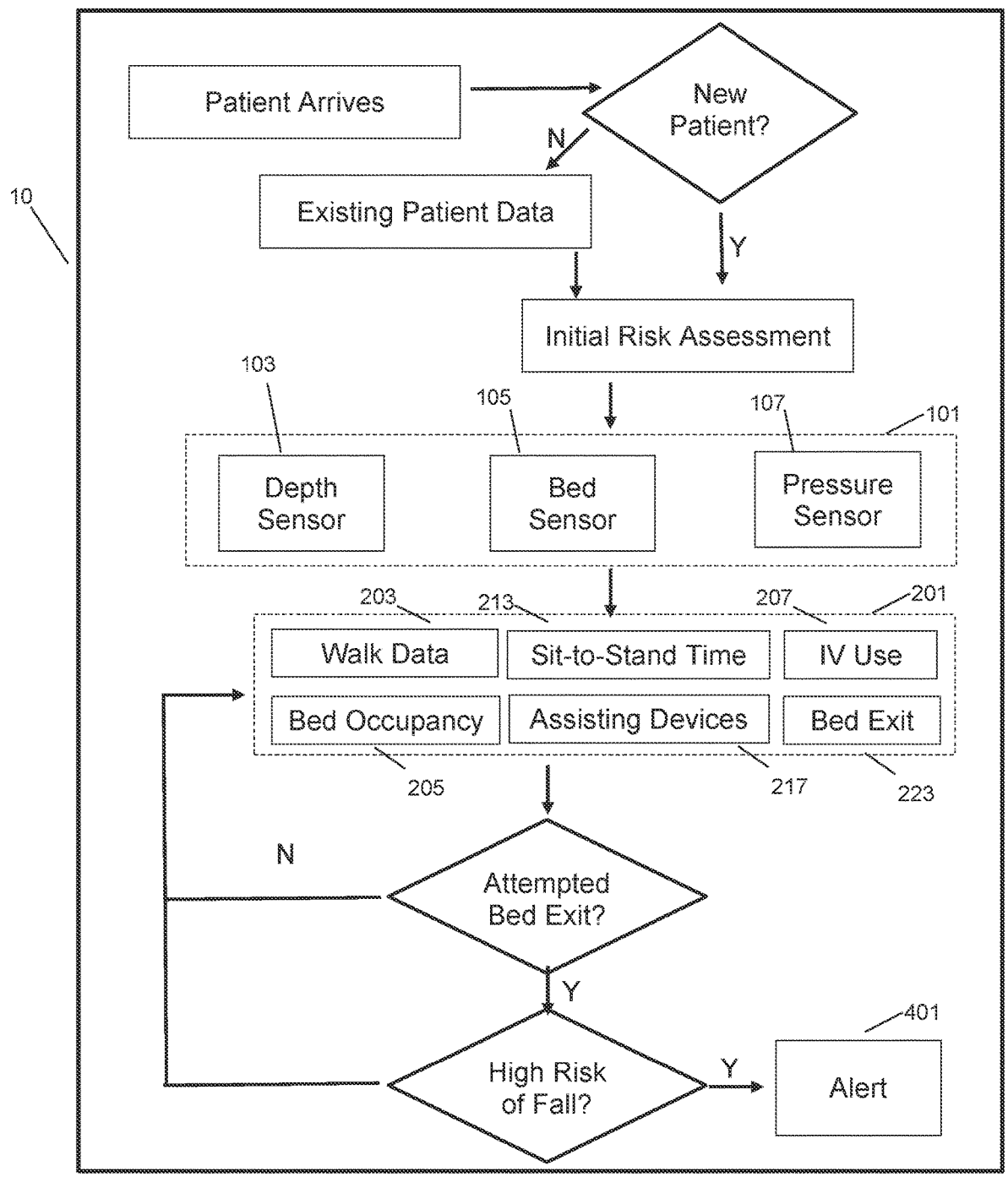
FIG. 2 depicts an embodiment of a method for the intelligent admissions systems and methods described herein.

The following description should be understood with respect to FIG. 1 and FIG. 2. FIG. 1 depicts an exemplary system for evaluating attempted bed exits based upon patient data. FIG. 2 depicts an exemplary embodiment of a method for evaluating attempted bed exits based upon patient data. The method depicted in FIG. 2 may be implemented using the systems depicted in FIG. 1 and the system depicted in FIG. 1 may implement the method depicted in FIG. 2 but neither of these is required.

In an embodiment, a determination of whether an attempted bed exit is occurring may be improved by a fall risk assessment performed independently on the patient to provide a base level of fall risk prior to the patient attempting a bed exit. However, it need not have been performed for the system to ascertain whether an attempted bed exit is occurring and generate an instantaneous risk assessment. Systems and methods for conducting a fall risk assessment are generally described in U.S. Utility patent application Ser. No. 15/248,810, filed Aug. 26, 2016, and U.S. Utility patent application Ser. No. 16/255,600, filed Jan. 23, 2019, the entire disclosures for both are incorporated herein by reference, including FIG. 1, and paragraphs [056] through [096] of Ser. No. 16/255,600.

Examining FIG. 1, and in settings where a bed is associated with the patient (either because they have residential facilities at the location or because they are at least at some point in time lying down on a bed assigned to them as is common in a hospital) a bed sensor (105) and/or pressure map sensor (107) may be used to detect when the bed is occupied (205), when the patient exits the bed (223), and the actions they take to attempt their bed exit (223). Bed sensors (105) and pressure map sensors (107) can, in an embodiment, be of the type described in U.S. patent application Ser. No. 13/600,539 and/or U.S. Provisional Patent Application Ser. No. 63/008,396, the entire disclosures of which are herein incorporated by reference. These types of sensors can provide details both that a patient is getting out of bed and about how they are getting out of bed. They can also be attached to other objects that a patient may lie or sit on such as, but not limited to, a chair, couch, or cushion as use of these objects, like a bed, generally indicate that a patient is not currently attempting locomotion when they are in them.

Bed sensors (105) as used herein will typically be devices which use characteristics of the bed itself to determine elements of a patient's actions on the bed. for example, movement of a mattress, compression of a mattress at specific points, mass being supported or displaced by the bed, etc. can be used to determine specifics about both the patient on the bed and actions being taken by that patient. This can include straight-forward detections such as, but not limited to, a patient's weight; to more subtle detections such as, but not limited to, their heartrate, body temperature, or respiratory rate; to specific detections such as, but not limited to, the speed of movement and instantaneous positioning and path of a patient's leg across a mattress surface, specifics of the time and motion for a patient to sit up from prone on the bed or to stand up from sitting on the edge of a bed, or specifics of a patient's use and positioning of a hand on the bed as a support.

Generally, a bed sensor (105) as contemplated herein is positioned on, under, or as part of a bed occupied by a patient that is being monitored. The bed sensor (105) will typically monitor the bed characteristics directly (e.g. the mattress temperature or acceleration detected relative to the bed frame), as opposed to the depth camera (101) which will typically monitor the patient more directly. However, a depth camera (101) may also detect changes to the bed. For example the depth camera (101) may "see" compression of the bed from a user shifting their weight.

The depth camera (101) and bed sensor (105) will work together, in an embodiment, to detect the specifics of a patient's movement and/or other factors that would indicate that a patient, based on how they are getting up, may be at an increased fall risk after getting up. Based on the risk determined, alerts may be issued to try and halt or slow the patient from getting up and/or to alert other personnel of a fall risk.

In any particular embodiment, how the system may determine the fall risk will depend on variables that the system has determined to be most informative for the monitored facility. However, these will generally fall into the broad categories of: being related to specifics of a patient's detected movement during the process of rising (from prone to standing), specifics of known risk factors related to external influencers on the patient (e.g. them awakening from the effects of anesthesia versus arising after natural sleep), and specifics of their gait and movement upon leaving the support of the bed.

The system will generally combine the data from both the depth camera (101) and bed sensor (105) to provide an increased understanding of the patient's movement while still on the bed, to allow for the system to, preferably, make risk determinations before the patient has reached a standing position beside the bed, before the patient has taken a step or tried to move from the support provided by standing at the bed, or before the patient has ambulated sufficiently far to fall. By making such a risk determination early and specifically for this patient, alerts can be provided which provide accurate risk assessment for this patient, preferably in real-time or near real-time, which can be used to halt the patient from proceeding with their attempted bed exit further, or from otherwise inhibiting ambulation or further ambulation.

In order to provide accurate information for the specific patient, the system (10) generally insure that the data, which is preferably de-identified from the patient, and is collected from them in an untethered fashion, is correctly connected with the patient. Depending on the setting (acute care, senior living, home), various computational algorithms may be used to separate data that belongs to the patient (i.e. the person to whom the bed "belongs") from data that belongs to other people in the field of evaluation that may be in common areas with the patient. This can include other patients, doctors, nurses, visitors, or cleaning staff, among others.

Often these separation algorithms will work on data from the camera (101) attempting to separate one person's image from another. However, knowing which image belongs to which person using computer image recognition from an image that has no identifiable information of the person is typically difficult and one of the primary benefits of a bed sensor (105) is that it can provide additional data to connect a patient to their record without need for such identification using identifiable data. As fall risk assessments are generated automatically continuously from data in the processor (301), they typically do not require patients to wear a device or be otherwise encumbered (which is only useful when the patient is wearing the device, and which can actually increase the risk of fall) and do not require human intervention beyond initially installing (and, when needed, maintaining) the sensors (101).

A bed sensor (105) can be used to determine if a bed is occupied (205) (which is a likely indicator that the individual is not subject to a current fall risk as they are lying down) and can also be used to determine specifics of the person's bed exit (223) behavior. It can also be used when parameters obtained from the depth image data (103) and bed sensor (105) relating to the patient are generally combined and processed together. For example, a patient who is known to have arrived in their room on a bed (e.g. from surgery) is clearly the patient in the bed when the room is first occupied. When an individual on the bed is later detected to be attempting to exit the bed, it is also highly likely that this is the patient and the fact that the patient is getting up can be used as a cue to access other relevant data about this patient in real-time. Thus, the bed sensor (105) data, while providing specifics both that the patient is attempting to get up and how they are attempting to get up, can also be used as a double check, or primary indicator, to identify the patient as a particular patient in the system (10) and access their records (313).

Another criteria (201) of assisting (217) and inhibiting (207) device use can be obtained either from entered records which are accessed when the patient is identified (e.g. that a doctor has indicated that the patient is currently connected to an IV or an initial check in screening indicated that the patient walks with a walker) or can be obtained from image data. For example, a patient attempting to rise or exit may be detected and data (313) loaded from the patient indicates that they walk with a walker. The image data may be scrutinized for an object that appears to be of the correct shape to that of a walker being near the point they are attempting to rise. Similarly, a bar of metal being detected as obscuring a patient's legs at the point one would expect the seat of a walker to be located would indicate that they are putting their legs down inside their walker.

The processor (301) can evaluate a patient's instantaneous fall risk based upon the data obtained from sensors. Data can be obtained from a bed sensor and can include such items as an individual's sit-to-stand time (213) (or generally how long it takes an individual to rise from a sitting position to a standing position) as well as items such as their current heart rate, respiration, or body temperature. A longer sit-to-stand time will generally indicate an increased fall risk as it indicates that the person is potentially rising unsteadily, or lacks leg strength. Further, items such as heart rate could indicate anxiety which could increase fall risk. Data from the sensors could be compared to prior data points collected for this individual since they entered the room, or could be compared against prior data from a patient's medical records, or general information about patients of similar characteristics.

A second criterion for fall risk can be the individual's typical walking speed and gait (203). An individual walking faster and more confidently will generally be at a reduced fall risk to one who shuffles or moves unsteadily. Similarly, patterns of gait or walk can also indicate increased fall risk. For example, a short shuffle may be associated with a patient with Parkinson's Disease, which disease may in turn be associated with increased fall risk and hesitation to start ambulating may also indicate an increased fall risk as the person is steadying themselves against the bed.

Such steadying behavior may be correlated from the camera (101) detecting hesitation and the bed sensor (105) detecting increased point pressure which could be the use of a hand compensating and accepting weight of the patient from the legs. The data can be further correlated by recognizing that the camera (101) detects the patient's arm against the bed where the point pressure increase is detected.

Prior gait information may have been obtained from sensors such as depth cameras (101) when the patient first entered the room. This could be particularly useful for patients that have had gait changes over their stay as it may show trends on fall risk over time. For example, a patient who is pregnant at admittance would likely have an increased fall risk (and different gait) than the same patient multiple days after giving birth (e.g. at discharge) but may have a decreased fall risk (and different gait) compared to the same patient in the immediate hours after giving birth when anesthesia may be wearing off. This patient may have different fall risk assigned as the system assesses their gait upon arrival compared to a gait when they were last assisted in walking to determine how well they are improving and if their risk should be lowered the next time they get up. This can allow patients that have improved gait (or returning to normal gait) to potentially be allowed to walk without assistance after sufficient improvement.

A third criterion is the patient's connection or exposure to stability inhibiting (207) or assisting (217) objects. A common stability inhibitor is a connection to an IV bag (207) or other object or machine which can hinder standard motion to which the patient is connected. These can show that a person is forced to carry out more complicated walking actions in order to move which increases fall risk. For example, being tethered to an IV bag provides an individual with a ready support device (although not a particularly good one), but also requires them to concentrate and move the IV support while they are walking which makes walking much more complicated. Detecting an attempt to remove an IV while attempting to stand or walk (as could be seen from an image camera showing a user touching the IV connection point, for example) could also show increased instability or fall risk as the patient is apparently concerned that the IV is inhibiting them.

Alternatively, if a patient is using an assistive device (217) such as a cane or walker, while this may indicate that the person has a generally increased long term fall risk, their short term fall risk is usually decreased as the device's purpose is specifically to inhibit falls and if they are used to and appearing to use it can indicate a decreased fall risk. At the same time, the systems an method may be able to determine that the assistive device is actually incorrectly suited to the individual (for example, the walker is not at a correct height for exit from the particular bed or has itself fallen over) and is actually increasing fall risk due to its unsuitability.

In addition to the above, additional criteria to be examined can include if it is typical for this individual to be currently attempting a bed exit (223) and the length of bed occupancy which is also tied to the frequency of exit (205). A person who has spent long periods of time in bed will likely have an increased fall risk and a person who regularly gets up may also have an increased fall risk as they are simply more exposed to the possibility of falls. Similarly, a person who is getting up atypically may also have an increased risk. For example, an individual getting up at night who has not gotten up at night before may be at an increased risk due to darkness. However, these criteria (or any subset of the criteria) can be evaluated without any prior data, processed through a machine learning algorithm (315) and compared with data compiled over a number of years. The system server (301) can determine when the particular values are being obtained for an individual it has evaluated before (and therefore provide results based on that particular individual) but can also assess the data for macro patterns within groups or the population of individuals (e.g. for males over the age of 65 who have had hip replacements).

For the critical question of whether a bed exit is being attempted, bed sensor (105) and pressure sensor (107) information can be used to determine if the patient is exhibiting a particular type of weakness (e.g. they appear to be moving a leg with their hand as opposed to moving it under its own power) which can indicate increased or decreased fall risk, as well as simply determining that the person is attempting to rise versus simply rolling over. This may also be combined with depth camera and/or thermal imagery of the bed to determine the motion of the individual.

It is an important aspect of the system to recognize that a patient that is lying down or sitting generally has a very low instantaneous fall risk. Conversely, an individual who is attempting to exit is at a risk of actually exiting, and thus at an increased risk of falling. Bed sensor (105), pressure sensor (107), and other sensor information can evaluate whether this is occurring in real time, regardless of whether additional data is known for this particular patient.

Once the instantaneous fall risk has been evaluated, the risk can be presented to a user (501) through a variety of interfaces (401). In a hospital setting, for example, the instantaneous fall risk of a patient (i.e., that the patient is currently attempting to get out of bed) may be provided to a nurse's monitoring station (411) for a floor or wing of a hospital in real-time or near real-time to allow them to quickly respond to a potentially high risk situation being detected. This allows the nurses to know that a patient is active and, in the event they are determined to be a higher fall risk, may need nursing or other staff to go assist them in a very short time frame. Alternatively, the user themselves may receive a notification by the system to inhibit risk. For example, an interface (401) may provide a recorded statement to the user (501) telling them to stay seated on the bed and not attempt to stand until a nurse arrives to avoid falling. When this is combined with quick nurse response (due to their notification) the patient is much more likely to be willing to wait for assistance. The system can also provide for mechanical intervention. This can include actively restraining a patient at particularly high fall risk until a nurse can arrive or can be as simple as illuminating the room to decrease the risk.

Taken together, it can be possible based upon data obtained in real time, to determine whether a bed exit is being attempted, and whether such an exit is dangerous (i.e., being conducted by an individual with a high risk of falling) or not. If the attempted exit is dangerous, a notice can be made, which can be evaluated by appropriate staff, and where necessary, an intervention can occur. If the attempted exit is not dangerous, staff need not be tasked to intervene and the patient's freedom of movement need not be curtailed.

An attempted exit can result in a successful exit quickly for some patients. Often a quick ability to exit will actually indicate a decreased risk of fall. In that situation, the system can determine whether, following the successful exit, a walking sequence is identifiable. Whether an exit is indicated, a walking sequence is identified, and a bed is not occupied (based upon path history of an object moving away from the bed at the time of the bed exit), it can be assumed it is a patient walking and not falling. This too can result in either action or inaction of staff. Such an evaluation is particularly useful for individuals who may not be a fall risk, but are a wandering risk and can provide a second level of protection where a patient fall is at least detected, even if it could not be prevented.

Referring now to FIG. 2, the system of FIG. 1 generally is operated as follows. The system (10) will generally first identify if this is a new patient, either through the entry of admissions data, through electronic medical records, or through admission algorithms which can either identify the patient as having previously been identified in the system or which has not previously been seen. Once identified (either as a previously existing patient or new), the system (10) will begin obtaining new data on the patient to use in the risk assessment. Further, the system (10) can also take in objective or subjective fall risk criteria entered by admittance personnel. For example, if the patient is indicated to walk with a cane, the system can now look for one and to evaluate the patient's gait based upon the gait of people who walk with canes.

Fall risk assessment may be based on data points or criteria (201) as described in the previous section. Such data points may include: data from identified walking sequences belonging to the patient (203), data from sit-to-stand motions belonging to the patient (213), data indicating if the patient was tethered to an IV (207) or uses an assisting device (217), and bed occupancy (205) and bed exit (223) data. The system (10) can identify which data belong to the patient and which are generated by others in the room based on monitoring bed exits (223) and bed entries as described previously. However, some or none of this data may be available at the time of an attempted bed exit and the system will typically make a determination based on the data it has, often erring on the side of inhibiting bed exit if the risk is unclear. However, the system may constantly update its fall assessments with new data during the patient's stay based on any or all available data and, therefore, is likely to become more accurate the longer the patient is monitored.

Once a patient is placed in a bed or chair, at a healthcare facility or in their own home, they could have an attempted bed exit. Data for that individual which previously exists in the system can be utilized to determine a fall risk, or general data can be used to ascertain whether the individual is in danger of a fall, particularly data from a bed sensor (105) and pressure sensor (107).

The available data is used to determine what the patient's current fall risk is, and whether the patient is currently attempting a bed exit. If the patient's calculated fall risk is expected to be high before any attempt at bed exit is made (for example, if they are awakening from anesthesia) and it is detected that they may be attempting a bed exit (for example, because they just awoke and may be confused), a notice can be provided in real time to available health care staff who can intervene as appropriate before the exit attempt is allowed to progress for any substantial time period.

As this intervention can preferably occur before the patient actually gets out of bed (or a chair) the system can actually inhibit a potential fall before it can happen, as opposed to simply notifying staff that a high risk individual has gotten up. Further, where a fall risk is high, but no bed exit is occurring, or where fall risk is low, no intervention is necessary (unless a patient's bed exit is itself a risk).

However, in addition to this predetermination of high risk leading to an alert in any attempted bed exit, the nature of the bed exit may also alter the calculation. For example, if a patient at a low calculated risk of fall is attempting a bed exit and the nature of the exit indicates that there is a heightened risk at this particular time, that may also trigger an alert. For example, a patient in a nursing home may regularly walk with a cane and is deemed to be at low risk if they use the cane. However, the system may detect that they are exiting and detect that they have just hit their cane while getting up and it has moved out of their reach (as indicated by a camera image detecting the movement of the cane, for example). The detected movement of the cane away from them may trigger an alert for this patient for this particular bed exit notifying that patient not to attempt to get their cane and that a nurse is on their way to help them.

Similarly, if a patient at low risk suddenly has a very different sitting up pattern or a different sit-to-stand pattern, this may trigger an alert as something may have happened to the patient in bed. For example if a patient is suddenly using their hands to swing a leg around having never done that before (as detected by a bed sensor or thermal imaging, for example) the system may trigger an alert to nursing personnel. As such action could indicate anything from a temporary issue of their leg having fallen asleep to a more serious one such as a partial loss of body function due to a micro stroke (for example) this type of detected change could notify not just assistance personnel for helping the patient get up, but more specialized personnel to perform further evaluations.

These types of individual alert where a patient's risk assessment is changed based on particular detected elements or pattern changes with the specific bed exit provide for increased robustness in fall protection. The system, in various embodiments, does not just detect bed exit by those placed in high risk categorically, but determines fall risk for each specific bed exit taking into account categorization of risk before the exit is attempted and also specific actions in this particular exit which would alter that determination. This combination can allow for a system which serves to inhibit falls by providing specific risk of a patient falling during or before ambulation after this bed exit, and inhibiting the patient from getting up without assistance should that instantaneous risk be deemed sufficiently high. It also reduces or eliminates the need for such assistance to be called if the patient is of sufficiently low risk during this exit to warrant such assistance.

While the invention has been disclosed in conjunction with a description of certain embodiments, including those that are currently believed to be useful embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

It will further be understood that any of the ranges, values, properties, or characteristics given for any single component of the present disclosure can be used interchangeably with any ranges, values, properties, or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

The qualifier "generally," and similar qualifiers as used in the present case, would be understood by one of ordinary skill in the art to accommodate recognizable attempts to conform a device to the qualified term, which may nevertheless fall short of doing so. This is because terms such as "spherical" are purely geometric constructs and no real-world component or relationship is truly "spherical" in the geometric sense. Variations from geometric and mathematical descriptions are unavoidable due to, among other things, manufacturing tolerances resulting in shape variations, defects and imperfections, non-uniform thermal expansion, and natural wear. Moreover, there exists for every object a level of magnification at which geometric and mathematical descriptors fail due to the nature of matter. One of ordinary skill would thus understand the term "generally" and relationships contemplated herein regardless of the inclusion of such qualifiers to include a range of variations from the literal geometric meaning of the term in view of these and other considerations.

The invention claimed is:

1. A system for determining the risk of a patient falling after exiting a bed, the system comprising:
   a bed including a bed sensor therein for monitoring a bed that is occupied by a patient;
   a depth camera for imaging said patient; and
   a computer running appropriate software to:
      determine movement specifics of how said patient moves immediately prior to exiting said bed from both said bed sensor and said depth camera;
      compare said movement specifics against stored movement specifics previously determined by said bed sensor and said depth camera from a prior movement of said patient immediately prior to exiting said bed to detect changes in a movement pattern of said patient immediately prior to exiting said bed;
      based on said changes in said movement pattern immediately prior to exiting said bed, evaluate a patient's instantaneous risk of falling after exiting said bed;
      if said instantaneous risk is sufficiently high, inhibiting said patient from exiting said bed; and
      if said instantaneous risk is not sufficiently high, allowing said patient to exit said bed uninhibited.

2. The system of claim 1, wherein said computer determines from said bed sensor that said patient is attempting to exit said bed.

3. The system of claim 2, wherein said computer obtains from said bed sensor at least on of said patient's current heart rate, respiration, or body temperature.

4. The system of claim 1, wherein said computer determines from said depth camera if an assistive device of said patient is within reach of said patient.

5. The system of claim 1, wherein said computer determines from said depth camera if said patient is connected to an IV line.

6. The system of claim 1, wherein said computer determines from said depth camera that said patient is attempting to get up.

7. The system of claim 1 wherein said computer obtains data was generated from said patient previously walking before entering said bed.

8. The system of claim 1, wherein said computer obtains data from said bed sensor to data for patients who previously fell.

9. The system of claim 1, wherein said computer obtains data from said depth camera to data for patients who previously fell.

10. The system of claim 1, wherein said computer evaluates data from said depth camera to determine said patient's walking speed.

11. The system of claim 1, wherein said computer evaluates data from said depth camera to determine said patient's gait while walking.

12. The system of claim 1 wherein said inhibiting comprises an alert made to medical personnel caring for said patient.

13. The system of claim 1 wherein said inhibiting comprises an alert made to said patient.

14. A method for determining the risk of a patient falling after exiting a bed, the method comprising:
   providing a bed including a bed sensor therein for monitoring a bed is occupied by a patient;
   providing a depth camera for imaging said patient;
   determining movement specifics of how said patient moves immediately prior to exiting said bed from both said bed sensor and said depth camera;
   comparing said movement specifics against stored movement specifics previously determined by said bed sensor and said depth camera from a prior movement of said patient immediately prior to exiting said bed to detect changes in a movement pattern of said patient immediately prior to exiting said bed;
   based on said changes in said movement pattern immediately prior to exiting said bed, evaluating a patient's instantaneous risk of falling after exiting said bed;
   if said instantaneous risk is sufficiently high, inhibiting said patient from exiting said bed; and
   if said instantaneous risk is not sufficiently high, allowing said patient to exit said bed uninhibited.

15. The method of claim 14 wherein said movement specifics include said bed sensor determining that said patient is attempting to exit said bed.

16. The method of claim 14 wherein said movement specifics include said depth camera determining that said patient is attempting to exit said bed.

* * * * *